United States Patent [19]

Sironi et al.

[11] Patent Number: 5,373,725
[45] Date of Patent: Dec. 20, 1994

[54] O-FID ANALYTICAL EQUIPMENT AND METHOD

[75] Inventors: Albino Sironi, Pozzo D'Adda (MI); Giuseppe Verga, Milan, both of Italy

[73] Assignee: Fisons Instruments S.p.A., Italy

[21] Appl. No.: 238,578

[22] Filed: May 5, 1994

Related U.S. Application Data

[63] Continuation of Ser. No. 959,650, Oct. 8, 1992, abandoned.

[30] Foreign Application Priority Data

Oct. 25, 1991 [IT] Italy .............................. MI91A002840

[51] Int. Cl.[5] .......................... B01J 29/04; G01N 1/22
[52] U.S. Cl. .................................. 73/23.39; 73/23.35; 73/23.38; 502/67; 502/61; 502/71; 422/78; 422/89; 422/93
[58] Field of Search ............... 73/23.29, 23.35, 23.38; 422/83, 78, 89, 93; 502/67, 61, 71

[56] References Cited

U.S. PATENT DOCUMENTS

| | | | |
|---|---|---|---|
| 3,224,838 | 12/1965 | Evans et al. | 422/93 |
| 3,607,075 | 9/1971 | Wolf et al. | 422/89 |
| 3,692,492 | 9/1972 | Poli et al. | 23/232 E |
| 3,790,348 | 2/1974 | Bossart et al. | 23/254 EF |
| 3,804,595 | 4/1974 | Scott | 422/83 |
| 4,077,775 | 3/1978 | LaCroix et al. | 422/78 |
| 4,111,554 | 9/1978 | Colin et al. | 73/23.35 |
| 4,135,881 | 1/1979 | Bakx et al. | 422/89 |
| 4,159,894 | 7/1979 | Hu | 422/78 |
| 4,193,964 | 3/1980 | John | 422/90 |
| 4,295,856 | 10/1981 | Anderson | 422/89 |
| 4,325,907 | 4/1982 | Dembicki, Jr. et al. | 422/89 |
| 4,466,943 | 8/1984 | Murase et al. | 422/89 |
| 4,732,881 | 3/1988 | Le Van Mao | 502/71 |
| 4,772,378 | 9/1988 | Miyauchi et al. | 208/107 |
| 4,784,833 | 11/1988 | Martin et al. | 422/80 |
| 4,805,441 | 2/1989 | Sides et al. | 73/23.39 |
| 4,981,652 | 1/1991 | Ratfisch | 422/54 |
| 5,002,894 | 3/1991 | Shakkottai et al. | 436/128 |
| 5,012,052 | 4/1991 | Hayes | 250/282 |
| 5,179,054 | 1/1993 | Schipper et al. | 502/67 |
| 5,264,183 | 11/1993 | Ebner et al. | 422/83 |

OTHER PUBLICATIONS

Werner Schneider et al., "Selective Gas Chromatographic Analysis of Oxygen-Containing Compounds by Flame Ionisation Detection", *J. of Chrom.*, 245 (1982) *Organic Chemistry*, Stanley H. Pine et al., 1980, pp. 20, 21, 531.

Primary Examiner—Hezron E. Williams
Assistant Examiner—J. David Wiggins
Attorney, Agent, or Firm—Lerner, David, Littenberg, Krumholz & Mentlik

[57] ABSTRACT

An anlytical equipment and method for the selective detection of individual oxygenated compounds in complex organic mixtures, in particular fuels, comprising, downstream an equipment of chromatographic separation, a cracking reactor, a catalytic hydrogenation microreactor and a FID detector. The cracking reactor is provided with a catalyst under the form of metal elements, made of palladium, inserted inside the capillary tube though which flows the gas under test. Thanks to the present equipment, the analytical process, based on the specific response of oxygenates to the method of flame ionization detection (O-FID), foresees that the cracking reaction takes place at temperatures below 1000 degrees C. and, consequently allows to keep the cracking reactor at stand-by temperatures below 700 degrees C.

34 Claims, 1 Drawing Sheet

O-FID ANALYTICAL EQUIPMENT AND METHOD

This is a continuation of application Ser. No. 07/959,650 filed Oct. 8, 1992, now abandoned.

BACKGROUND OF THE INVENTION

1. Field of the Invention

The present invention relates to an analytical equipment and method for the selective detection of individual oxygenated compounds in complex organic mixtures, specially for fuels of the recent type that use oxygenated compounds, instead of lead, to increase their antiknock value (octane rating).

The already known analytical equipments of the type considered in the present invention are based on the specific response of oxygenates substances to the methods of flame ionization (O-FID) detection and comprise, downstream an equipment of chromatographic separation, a cracking reactor constituted by a capillary tube through which the gas under test flows, said tube being made of a platinum and rhodium alloy that is heated to high temperatures as well as, downstream, a catalytic hydrogenation microreactor and a flame ionization detector (FID).

In the cracking reactor, which is directly connected with the capillary column of chromatographic separation, the cracking reaction takes place, during which the individual oxygenated compounds, selectively eluted in sequence by the capillary column, are transformed into carbon monoxide according to the known reaction:

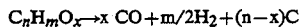

$$C_nH_mO_x \rightarrow x\,CO + m/2\,H_2 + (n-x)C$$

while hydrocarbons constituting the organic matrix are converted into carbon and hydrogen.

As known (see Werner Schneider et al. "Journal of Chromatography" 245, 1982, 71-83; G. R. Verga and A. Sironi "Journal of High Resolution Chromatography & Chromatography Communications" Vol. 11, March 83, pages 248-252) said reaction takes place, in the equipments of the prior art, at temperatures of 1100–1300 degrees C., since the presence of a carbon layer (under the form of graphite) on the internal walls of the platinum/rhodium capillary tube is required for the correct performance of each analysis. The absence of said arrangement could involve, besides the already mentioned reaction, other reactions that would generate compounds different from the desired ones (for instance $CO_2$ instead of CO) and, consequently errors or in any case lack of analytical precision.

In known equipments the carbon layer on the walls of the platinum/rhodium capillary tube is obtained by continuously enriching the carrier gas with some parts per million (ppm) of hydrocarbon, by means of an appropriate doping system, or by injecting into the equipment a suitable quantity of hydrocarbon before each analytical cycle.

Furthermore, in the time intervals between a series of analyses and the subsequent one, the cracking reactor is never brought to room temperature but kept at temperatures not going below 700 degrees C.

This precaution is necessary in order to avoid long idle times between one analysis and the following one and to avoid considerable sudden changes of temperature in the cracking reactor that would decrease the operating life of the capillary tube.

High operating and stand-by temperatures of the cracking reactor as well as the need of introducing a carbon excess cause a gradual deterioration of the platinum/rhodium capillary tube, that therefore must be replaced every 1000 hours of operation on the average: the replacement of the capillary tube involves dead times and outstanding costs, mainly because of the high cost of rhodium.

OBJECTS OF THE INVENTION

An object of the present invention is now to provide an analytical equipment of the afore defined type, for the selective detection of individual oxygenated compounds, that provides a higher average operating life of said capillary tube of the cracking reactor and/or a consequent operating cost that is lower than that of the equipments of the prior art.

SUMMARY OF THE INVENTION

This object is achieved by means of the present invention that concerns an analytical equipment for the selective detection of individual oxygenated compounds in complex organic mixtures, in particular fuels, of the type comprising, downstream an equipment of chromatographic separation, a cracking reactor consisting of a capillary tube through which the gas under test flows, said tube being made of a platinum/rhodium alloy and heated to high temperatures, a microreactor of catalytic hydrogenation and a flame ionization detector (FID), characterized in that said capillary tube contains one or more metal catalysts, in particular made of palladium and/or its alloys.

The presence of said one or more catalysts can be obtained in different ways, for example and with no restricting purposes, palladium may be present as thin layer on the internal surface of the platinum/rhodium capillary tube, or may be introduced into said tube under the form of small particles, powders, sponges, wire gauzes and filaments.

Therefore using said palladium-based catalysts it is possible to considerably reduce the operating and stand-by temperatures of the cracking reactor, obtaining as a consequence an increase of the average operating life of the capillary tube, corresponding to about 5 times the average duration obtainable according to the known technique.

Another advantageous feature of the present invention, related to the first one, concerns the reduction of rhodium content in the alloy forming said capillary tube, which involves a significant decrease in the operating costs of the analytical equipment: the rhodium percentage in the alloy constituting the capillary tube may be reduced up to actually zero.

A third advantageous feature concerns the fact that, during the stage of activation of the palladium catalysts, it is possible to incorporate carbon into the atomic lattice of palladium itself. In this way the use of the continuous hydrocarbon doping system results unnecessary, since the required carbon amount is provided by the very samples to be analyzed and is properly retained by the palladium catalysts.

The invention also concerns an analytical method that, by means of an equipment such as the one described hereinabove, foresees the introduction of the sample to be analyzed into the equipment of chromatographic separation through an injector of the splitting type, and its subsequent passage into a separating capillary column under the action of a carrier gas (for instance $N_2$). The individual oxygenated compounds, selectively eluted by the separation capillary column, find themselves, each in a different moment, in the cracking reactor where the homonymous already mentioned reaction takes place.

According to an innovative aspect of the present invention, the cracking reaction, in the equipment presented herein, takes place at temperatures below 1000 degrees C. and, more precisely, at a temperature of approximately 800 degrees C.

Consequently, also the stand-by temperatures of the cracking reactor can be kept below 700 degrees C. and, more precisely, at a temperature of approximately 500 degrees C.

The present invention will be now described, for illustrative and non limiting purposes, with reference to the accompanying drawings, wherein:

DESCRIPTION OF THE PREFERRED EMBODIMENTS

Figure 1:
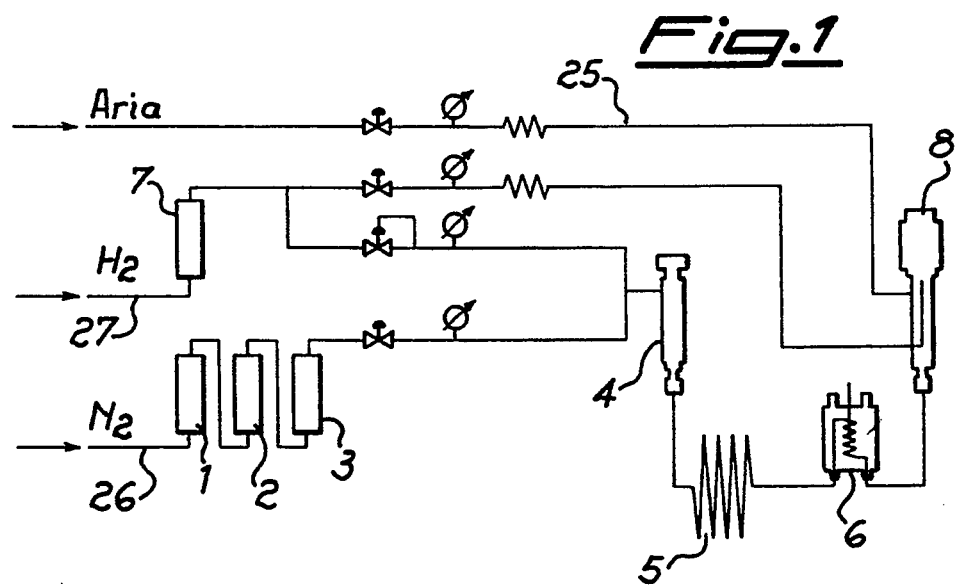
FIG. 1 is a schematic drawing of an O-FID analytical equipment according to a possible embodiment.

With reference to FIG. 1, the analytical equipment illustrated therein is essentially constituted by, an equipment of chromatographic separation, downstream which there are provided a cracking reactor 6 and a device 8 that, in the specific configuration shown, comprises a reactor of catalytic hydrogenation and a FID detector.

The equipment of chromatographic separation comprises a line 25 for air feeding directly connected with said device 8, a line 26 for carrier gas (e.g. $N_2$) feeding, along which there is provided a series of filters 1, 2, 3 to purify carrier gas from possibile oxygen compounds (for example, CO, $CO_2$, $O_2$, $H_2O$) connected with an injector 4 of the splitting type, a line 27 for auxiliary gas feeding e.g. $H_2$), on which there is provided a filter 7 (for $O_2$ and $H_2O$) connected with the device 8 and with the line 26 upstream the injector of the splitting type 4, and a separation capillary column 5.

Figure 2:
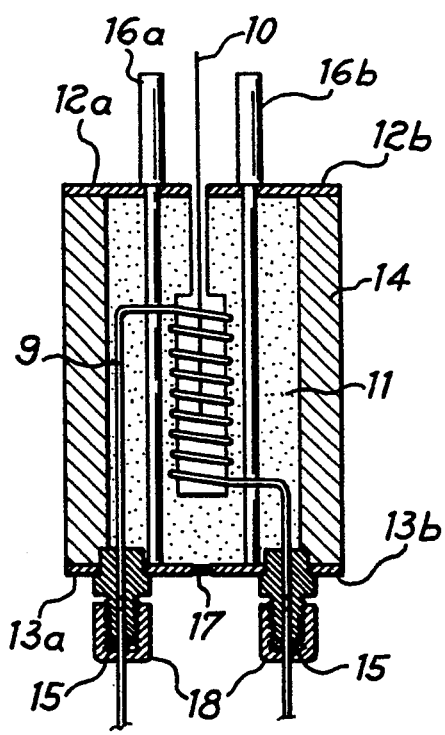
FIG. 2 is a partial sectional longitudinal view of a cracking reactor according to a possible embodiment.

With reference to FIG. 2, the cracking reactor 6 is enclosed in a container having side walls 14 made of marinite or other similar material, closed on the top by a couple of metal plates 12a, 12b and on the bottom by another couple of metal plates 13a, 13b; the metal plates 12a, 13a are electrically connected to one another and both to an electrode 16a projecting from the upper metal plate 12a, as well as plates 12b, 13b are electrically connected to one another and both to an electrode 16b projecting from the upper metal plate 12b.

Each of the lower metal plates 13a and 13b, separated by electrically insulating means 17, presents a connector 18, linking the cracking reactor to the separation capillary column 5 and to the catalytic hydrogenation microreactor, incorporated, according to a particular embodiment, in the device 8 together with the FID detector, the sealing being ensured by gaskets 15 generally made of graphite.

Inside, the cracking reactor 6 essentially comprises a capillary tube 9 heated to high temperature obtainable, for instance, by Joule effect through low voltage electric power supplied to the electrodes 16a and 16b, a thermocouple 10 being provided to sense a signal depending on the temperature, and means 11 electrically and thermally insulate the capillary tube 9 from the external environment.

Figure 3:
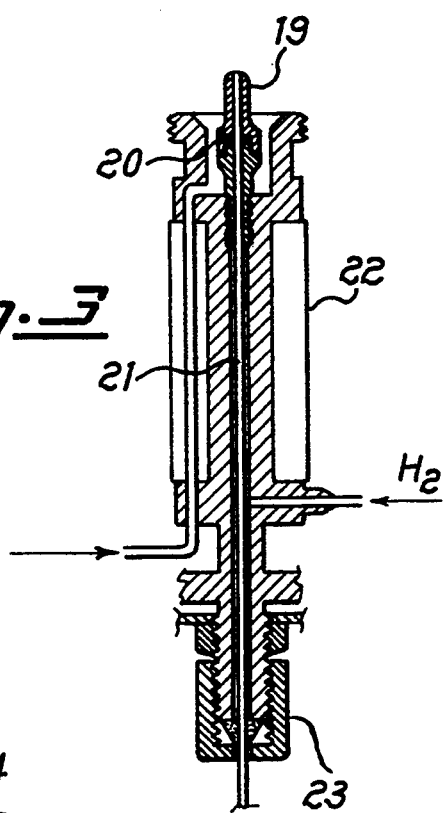
FIG. 3 is a sectional longitudinal view of the device that, according to a possible embodiment, incorporates the catalytic hydrogenation microreactor and the FID detector.

FIG. 3 shows a longitudinal sectional view of the device 8 that, according to an embodiment of the invention, incorporates a catalytic hydrogenation microreactor and a FID detector.

Said catalytic hydrogenation microreactor essentially consists of a short capillary tube 21 of the PLOT type made of glass, lined with a inner layer of aluminium oxide in which nickel is adsorbed as catalyzing element and heated by means 22 to obtain the temperatures required for the hydrogenation reaction of the carbon monoxide, the latter being supplied by the cracking reactor 6 through the connector 23.

Said FID detector consists of a nozzle 19 directly connected to said hydrogenation microreactor, sealing being ensured by gaskets 20 generally made of graphite.

Figure 4:
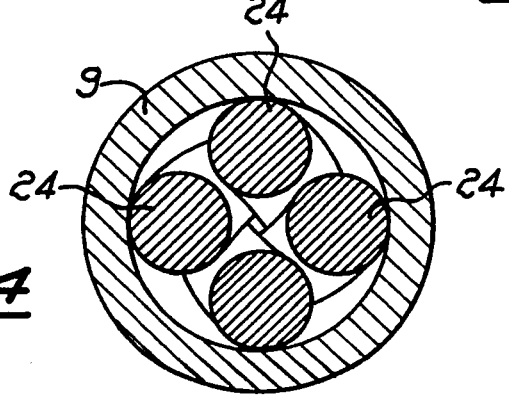
FIG. 4 is a magnified cross-sectional view of the capillary tube of the cracking reactor according to a possible embodiment of the invention.

FIG. 4 shows a cross sectional view of the capillary tube 9, inside which there are inserted, according to one of the possible embodiments of the invention, metal filaments of palladium 24 braided together.

After the replacement of the platinum/rhodium capillary tube 9 or eventually after a prolonged off period of the analytical equipment, it is or may be necessary to perform the activation of the palladium catalyzing elements 24 by means of a series of subsequent heating and cooling cycles in hydrogen atmosphere and, then, the hot saturation with hydrocarbon for carbon incorporation into the palladium atomic lattice.

During the use of the analytical equipment, the necessary carbon amount incorporated in palladium is supplied with the injection of the very samples to be analysed, thus allowing to avoid the presence of a doping system needed in the equipments of the known technique.

The presence of a catalyzing agent, under the form of said metal elements in palladium, inside the capillary tube 9 made of a platinum and rhodium alloy, makes a high rhodium content in the alloy superfluous, since average operating temperatures are 800 degrees C.

Furthermore, according to an advantageous feature of the present invention, the capillary tube 9 can even be realized without any rhodium content.

According to a further advantagenous feature of the present invention, the presence of said catalyzing elements 24 made of palladium allows a significant reduction of the operating temperatures in the cracking reactor 6, thus extending the average operating life of the capillary tube 9 and consequently decreasing the operating costs of the analytical equipment, moreover allowing to avoid the presence of a continuous hydrocarbon doping system.

We claim:

1. An apparatus for detecting oxygenated compounds in organic mixtures, said apparatus comprising:
    gas source means for providing at least one gas including said oxygenated compounds to be analyzed;
    cracking reactor means for providing a cracked product from said oxygenated compounds, said cracking reactor means arranged downstream of said gas source means and having a capillary tube therein, said capillary tube having an outer shell comprising platinum, said outer shell defining an outer diameter and an inner diameter, at least one catalyzing metal arranged within said inner diameter of said outer shell, whereby said at least one catalyzing metal is adapted to be exposed to gas provided by said gas source and thus facilitates a reduction in the operating and stand-by temperatures of said cracking reactor;

a catalytic hydrogenation microreactor arranged to communicate with said cracking reactor means for hydrogenating said cracked product; and a flame ionization detector adapted to detect said hydrogenated cracked product.

2. The apparatus of claim 1 wherein said at least one catalyzing metal comprises palladium.

3. The apparatus of claim 1 wherein said outer shell of said capillary tube further comprises a platinum-rhodium alloy.

4. The apparatus of claim 1 wherein said outer shell of said capillary tube has an internal surface defining an inner diameter, said at least one catalyzing metal forming a layer on said internal surface.

5. The apparatus of claim 1 wherein said at least one catalyzing metal is arranged within said inner diameter of said capillary tube.

6. The apparatus of claim 5 wherein said at least one catalyzing metal comprises filaments.

7. The apparatus of claim 3 wherein said capillary tube comprises a greater amount of said platinum than said rhodium.

8. The apparatus of claim 1 wherein carbon is incorporated into said at least one catalyzing metal.

9. The apparatus of claim 2 wherein said outer shell of said capillary tube further comprises a platinum-rhodium alloy.

10. The apparatus of claim 2 wherein said outer shell of said capillary tube has an internal surface defining an inner diameter, said palladium forming a layer on said internal surface.

11. The apparatus of claim 2 wherein said palladium is arranged within said inner diameter of said capillary tube.

12. The apparatus of claim 11 wherein said palladium comprises filaments.

13. The apparatus of claim 9 wherein said capillary tube comprises a greater amount of said platinum than said rhodium.

14. The apparatus of claim 2 wherein said carbon is incorporated into said palladium.

15. An apparatus for detecting oxygenated compounds in organic mixtures, said apparatus being adapted to crack said oxygenated compounds, said apparatus comprising a cracking reactor having a capillary tube therein, said capillary tube having an outer shell including platinum, said outer shell defining an outer diameter and an inner diameter, at least one metal catalyst arranged within said inner diameter of said outer shell whereby said at least one metal catalyst is adapted to be exposed to gas provided by a gas source and thus facilitates a reduction in the operating and stand-by temperatures of said crack reactor.

16. The cracking reactor of claim 15 wherein at least one catalyzing metal comprises palladium.

17. The cracking reactor of claim 15 wherein said outer shell of said capillary tube further comprises a platinum-rhodium alloy.

18. The cracking reactor of claim 15 wherein said outer shell of said capillary tube has an internal surface defining an inner diameter, said at least one catalyzing metal forming a layer on said internal surface.

19. The cracking reactor of claim 15 wherein said at least one catalyzing metal is arranged within said inner diameter of said capillary tube.

20. The cracking reactor of claim 19 wherein said at least one catalyzing metal comprises filaments.

21. The cracking reactor of claim 17 wherein said capillary tube comprises a greater amount of said platinum than said rhodium.

22. The cracking reactor of claim 15 wherein carbon is incorporated into said at least one catalyzing metal.

23. The cracking reactor of claim 16 wherein said outer shell of said capillary tube further comprises a platinum-rhodium alloy.

24. The cracking reactor of claim 16 wherein said outer shell of said capillary tube has an internal surface defining an inner diameter, said palladium forming a layer on said internal surface.

25. The cracking reactor of claim 16 wherein said palladium is arranged within said inner diameter of said capillary tube.

26. The cracking reactor of claim 25 wherein said palladium comprises filaments.

27. The cracking reactor of claim 23 wherein said capillary tube comprises a greater amount of platinum than said rhodium elements.

28. The cracking reactor of claim 16 wherein carbon is incorporated into said palladium.

29. A method of detecting oxygenated compounds in an organic mixture, said method comprising the steps of providing a cracking reactor including a capillary tube, said capillary tube having an outer shell comprising platinum, said outer shell defining an outer diameter and an inner diameter and having at least one catalyzing metal arranged within said inner diameter for providing a cracked compound from said oxygenated compounds after exposure to at least one gas including said organic mixture;

providing a catalytic hydrogenation reactor for hydrogenating said cracked compound;

exposing said at least one gas to said at least catalyzing metal within said inner diameter of said capillary tube and maintaining said cracking reactor at a temperature below about 1000° C.; and detecting said cracked hydrogenated compound by flame ionization detection.

30. The method of claim 29 wherein said cracking reactor is maintained at a temperature of about 800° C.

31. The method of claim 29 wherein said cracking reactor is maintained at a temperature below about 700° C.

32. The method of claim 29 further comprising the step of performing multiple analyses to detect said oxygenated compounds and multiple organic mixtures; and permitting a predetermined stand-by time to lapse between said analyses, whereby said temperature of said cracking reactor is maintained at a temperature of about 500° C. during said stand-by time.

33. The method of claim 29 wherein said at least one catalyzing metal comprises palladium, said method further comprising the step of activating said palladium by alternately heating and cooling said palladium under a stream of hydrogen and subsequently heating said palladium and saturating said palladium with hydrocarbon, whereby carbon is incorporated into the atomic lattice of said palladium.

34. The method of claim 33 wherein said organic mixture is injected into said capillary tube, said organic mixture is adapted to supply a sufficient amount of carbon to said palladium without the need for an external doping system.

* * * * *